United States Patent [19]

Anderson et al.

[11] Patent Number: 4,681,578
[45] Date of Patent: Jul. 21, 1987

[54] PANTILINER WITH VENTILATION AREAS

[75] Inventors: Arthur B. Anderson; Sherry L. Brandt, both of Hamilton, Ohio

[73] Assignee: The Procter & Gamble Company, Cincinnati, Ohio

[21] Appl. No.: 709,618

[22] Filed: Mar. 8, 1985

[51] Int. Cl.[4] .............................................. A61F 13/16
[52] U.S. Cl. .................................. 604/385 R; 604/387
[58] Field of Search ........................ 604/380, 386–387, 604/358, 378, 385.1

[56] References Cited

U.S. PATENT DOCUMENTS

| | | | |
|---|---|---|---|
| 2,964,040 | 12/1960 | Ashton | 604/366 |
| 3,426,754 | 2/1969 | Bierenbaum et al. | 128/156 |
| 3,463,154 | 8/1969 | Hendricks | 128/287 |
| 3,559,649 | 2/1971 | Grad | 604/382 |
| 3,559,650 | 2/1971 | Larson | 128/290 |
| 3,570,491 | 3/1971 | Sneider | 128/290 |
| 3,882,871 | 5/1975 | Taniguchi | 128/287 |
| 4,015,604 | 4/1977 | Csillig | 604/382 |
| 4,059,114 | 11/1977 | Richards | 128/287 |
| 4,241,462 | 12/1980 | Tagawa et al. | 2/406 |
| 4,333,463 | 6/1982 | Holtman | 604/378 |
| 4,341,216 | 7/1982 | Obenour | 128/287 |

FOREIGN PATENT DOCUMENTS 0104906  9/1983  European Pat. Off. ............ 604/378

Primary Examiner—John D. Yasko
Attorney, Agent, or Firm—Thomas J. Slone; Frederick H. Braun; Richard C. Witte

[57] ABSTRACT

An absorbent article such as a pantiliner provided with at least one ventilation area which allows the passage of vapor to provide cooling and drying effects so that the pantiliner is more comfortable to wear. The pantiliner is made up of a core, a relatively vapor pervious outer layer and a liquid impervious barrier layer interposed between the layer and the core. The barrier layer is essentially the same length as the pantiliner, but is a smaller transverse width in the end regions of the pantiliner so that at least one ventilation area is formed. The pantiliner can also be provided with an optional topsheet and an optional wicking layer.

28 Claims, 3 Drawing Figures

PANTILINER WITH VENTILATION AREAS

BACKGROUND OF THE INVENTION

1. Field of the Invention

This invention relates generally to absorbent articles such as pantiliners and, more particularly, to absorbent articles which permit the passage of vapor while retaining and retarding the passage of fluids.

2. Background Art

Absorbent articles such as sanitary napkins and pantiliners are well known for their use in absorbing and retaining liquid discharges from the human body. Sanitary napkins are used principally during a woman's menstrual period to contain menses and other vaginal discharges so as to protect garments from soiling. However, many women experience frequent or daily, light vaginal discharges between their menstrual periods. While sanitary napkins are an efficient way to deal with the problem, products such as pantiliners have been developed specifically to protect a woman's garments from soiling due to these light discharges and to provide supplemental protection for garments when other catamenial products are used during the menstrual period.

Pantiliners are generally small in size, absorbent and comfortable to use. Several references describe the use of such pantiliners. Generally, pantiliners are intended to be affixed to the crotch region of the user's undergarment and comprise an absorbent core, a topsheet, and an impermeable backsheet located on the pantiliner's garment-facing side that acts as a fluid barrier to absorbed body liquids so as to protect the user's garments from staining. For example, U.S. Pat. No. 3,463,154 issued to Hendricks on Aug. 26, 1969, discloses a disposable panty shield for undergarments which has an outer liquid repellent layer made from a plurality of thin sheets of vinyl or polyethylene to retain the liquid within the shield. U.S. Pat. No. 2,964,040 issued to Ashton et al. on Dec. 13, 1960, discloses an arcuate shaped pad with a water repellent layer to prevent liquid strikethrough of absorbed body fluids.

Because pantiliners are used for daily, light vaginal discharges, generally they are designed to be worn all day. However, because of the impermeable backsheet, conventional pantiliners can be hot and uncomfortable to wear for long periods of time. In addition, the impermeability of the backsheet precludes the pantiliner from self-drying which would otherwise occur through evaporation of the absorbed liquid.

Several absorbent devices have been developed which are pervious to vapor. Products which are pervious to vapor are generally known as "breathable". For example, U.S. Pat. No. 4,341,216 issued to Obenour on July 27, 1982, discloses a breathable backsheet constructed of a vapor pervious and liquid impervious outer sheet and a smaller length liquid impermeable inner sheet. U.S. Pat. No. 3,426,754 issued to Bierenbaum et al. on Feb. 11, 1969, discusses a breathable medical dressing constructed from a microporous polymer film.

Pantiliners are also known which provide a breathable backsheet. Generally, these pantiliners are provided with a fluid impervious, vapor permeable backsheet to allow the exchange of vapor while preventing the staining of the wearer's undergarment. For example, U.S. Pat. No. 4,059,114 issued to Richards on Nov. 22, 1977, discloses a disposable garment shield having a moisture barrier ply constructed of a blown microfiber web which is fluid impermeable but vapor permeable. European Patent Application No. 0 104 906 filed by Becker et al. on Sept. 23, 1983, and published Apr. 4, 1984, discusses a breathable panty liner having a fibrous, vapor permeable, liquid repellent outer layer.

While these "breathable" pantiliners do provide some measure of improvement over the more common "impermeable" pantiliners, comfort, garment staining, dryness, and vapor exchange (breathability) remain as key design considerations. Accordingly, devices providing for the better retention and absorption of liquids while providing for the more efficient passage of vapor have been sought.

It is, therefore, an object of the present invention to provide a "breathable" pantiliner.

It is a further object of this invention to provide a pantiliner with ventilation areas which allow the exchange of vapor thereby providing cooling and drying effects so that the pantiliner is more comfortable to wear.

It is a further object of this invention to provide a pantiliner which prevents fluid leakage from the most common areas of pantiliner soiling to protect the wearer's garments, while maintaining its ability to allow the exchange of vapor.

Other objects and advantages of the present invention will be apparent to one skilled in the art from the following description.

SUMMARY OF THE INVENTION

The present invention provides an absorbent article and, more particularly, a pantiliner which protects the user's garments from soiling, while being vapor pervious or breathable to allow the evaporation of retained body fluids thereby providing greater comfort to the user.

The absorbent article of the present invention is provided with at least one ventilation area to provide breathability for the absorbent article. The ventilation area is obtained by positioning a barrier layer of a relatively fluid impervious material between a core and a relatively vapor pevious outer layer. The barrier layer is substantially longitudinally coterminous with (i.e. of equal length to) the pantiliner but is a smaller transverse width in at least one of the end regions of the pantiliner. Therefore, part of the core located in the areas adjacent to the end regions of the pantiliner is covered by only the outer layer so that vapor and air may exchange through the relatively vapor pervious outer layer to and from these parts of the core thereby permitting evaporation of any vaginal discharges or other fluids that have been retained in the core. In addition, because the barrier layer is constructed of a relatively fluid impervious material, additional strikethrough protection is achieved in the middle region where the greatest amount of protection is required so that the user's garments are not soiled.

While the specification concludes with claims particularly pointing out and distinctly claiming the subject matter which is regarded as forming the present invention, it is believed that the invention will be better understood from the detailed description appearing in the following section taken in conjunction with the accompanying drawings.

Figure 1:
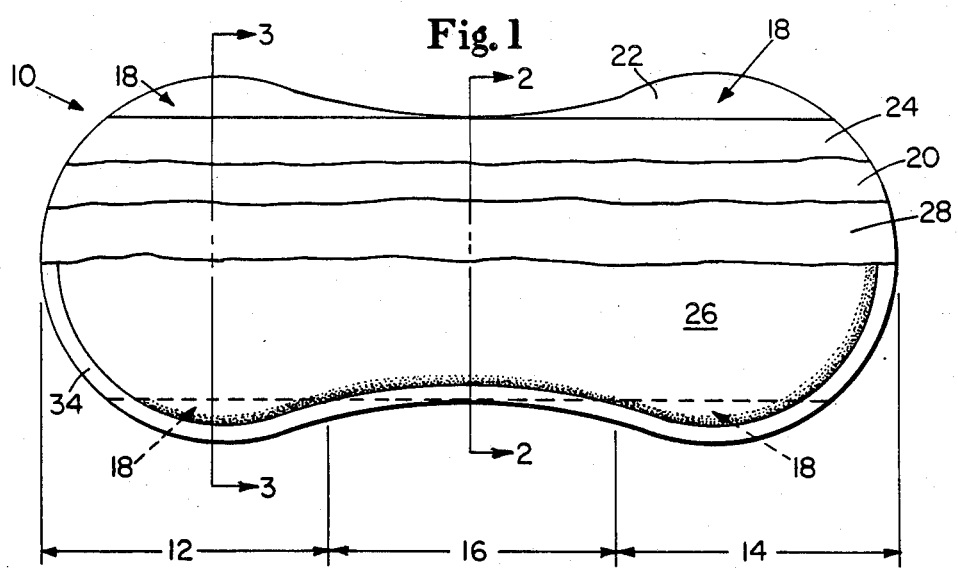
FIG. 1 is a top plan view of the pantiliner of the present invention with a partially cut-away section to illustrate the configuration of the barrier layer, the outer layer and the absorbent core which form the ventilation areas.

In the drawings the thicknesses of certain materials have been exaggerated for clarity. In the various figures, reference numerals are used consistently to refer to identical or equivalent elements.

DETAILED DESCRIPTION OF THE INVENTION

Figure 2:
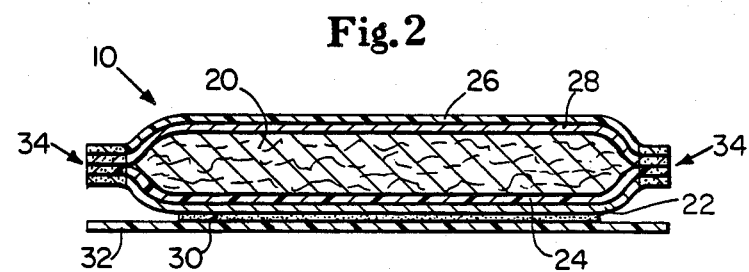
FIG. 2 is a cross-sectional view of the pantiliner shown in FIG. 1 taken along line 2—2 of FIG. 1.
Figure 3:
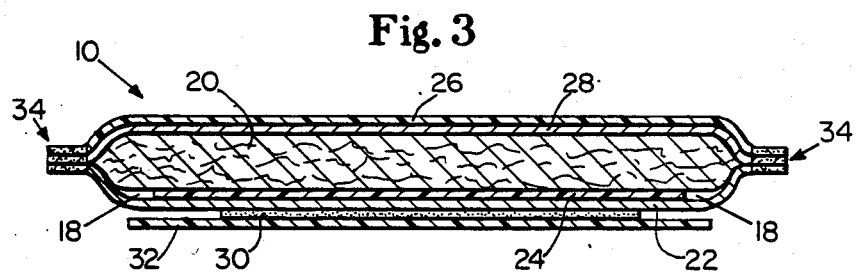
FIG. 3 is a cross-sectional view of the pantiliner shown in FIG. 1 taken along line 3—3 of FIG. 1.

A preferred embodiment of the absorbent article of the present invention, pantiliner 10, is shown in a partially cut-away front plan view in FIG. 1 and in cross-sectional view in FIGS. 2 and 3. The pantiliner 10 consists of two end regions 12 and 14, a middle region 16, and at least one ventilation area 18 which is adjacent to at least one of the end regions 12 and 14 of the pantiliner 10. The pantiliner 10 has a body-facing side that is in contact with the user's body and a garment-facing side that is in contact with the inner surface of the user's undergarment.

While the pantiliner 10 may have any shape known in the art, including those of diapers or sanitary napkins, a preferred shape tapers inwardly from a relatively greater transverse width in a portion of one of the end regions 12 and 14 to a relatively smaller transverse width at the middle region 16. Transverse width is generally defined as the dimension perpendicular to the dimension, which is defined as length, running from end region 12 to end region 14. An especially preferred shape tapers inwardly such that a portion of both end regions 12 and 14 are a relatively greater transverse width than the middle region 16, with the most preferred shape being a nonlinearly inwardly tapering shape such as is shown in FIG. 1.

To retain absorbed fluid in the interior of the pantiliner 10 and to provide some measure of fluid absorbency, the pantiliner 10 is provided with a core 20. The core has a garment-facing side and a body-facing side. The core 20 may be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, a web of polymeric fibers, and a blend of polyester and polypropylene fibers.

Preferably, the core comprises a mass or batt of fibers. While many types of fibers may be used, a preferred material is a batt of polyester fibers.

To provide a degree of softness and a vapor pervious covering for the garment-facing side of the pantiliner 10, an outer layer 22 is provided adjacent the core 20 on the garment-facing side of the core 10. The outer layer 22 must be vapor pervious so that vapor can exchange through the outer layer 22. While the outer layer 22 can be formed from any vapor pervious material known in the art, a preferred material is a soft, smooth, compliant, liquid and vapor pervious material. Those skilled in the art may readily select woven and nonwoven materials useful for this purpose, though nonwoven materials are preferred. For example, porous materials used as topsheets for disposable diapers or as coverings for conventional sanitary napkins can be used in the present invention. Useful outer layers 22 are described in U.S. Pat. No. 4,341,217 issued to Ferguson and Landrigan on July 27, 1982, and U.S. Pat. No. 4,342,314 issued to Radel and Thompson on Aug. 3, 1982, both patents being incorporated herein by reference.

Interposed between the core 20 and the outer layer 22 is a barrier layer 24. The barrier layer 24 prevents fluids retained by the core 20 from striking through the pantiliner 10 and soiling adjacent garments. Therefore, the barrier layer must be fluid impervious. Suitable materials are well known in the art, including woven and nonwoven fabrics which have been treated to render them liquid repellent. Breathable or vapor pervious, liquid resistant materials, and those materials described in U.S. Pat. No. 3,881,489 issued to Hartwell on May 6, 1975 and U.S. Pat. No. 3,989,867 issued to Sisson on Nov. 2, 1976 can also be used. These patents are incorporated herein by reference. Preferred materials are those materials that are fluid and vapor impervious, because they provide additional fluid strikethrough protection. Especially preferable materials include formed thermoplastic films. One especially suitable material is a polyethylene film having a thickness of from about 0.075 mils to about 1.25 mils, with a 1.0 mil thickness polyethylene film being especially suitable.

The shape of the barrier layer 24 is a key factor in forming the ventilation areas 18. The shape of the barrier layer 24 generally determines the number, size and location of the ventilation areas. While the barrier layer 24 is substantially longitudinally coterminous with (i.e. the same length as) the pantiliner 10, the barrier layer 24 must at least have an area in either of the end regions 12 and 14 which is of a lesser transverse width than that end region 12 and 14, so that at least one ventilation area 18 is formed adjacent to that end region. Therefore, the barrier layer 24 may generally be of any shape that conforms to the above description.

A preferred shape of the barrier layer 24 is as shown in FIG. 1. The barrier layer has essentially a uniform transverse width. In addition, the barrier layer 24 has an even more preferred shape in which the uniform width is substantially the same transverse width as the narrowest portion of the middle region 16 of the pantiliner 10. With this preferable configuration, four ventilation areas 18 are formed in the pantiliner 10.

The barrier layer is preferably secured to the other elements at the end regions 12 and 14 of the pantiliner 10. Because the barrier layer 24 is secured at the end regions 12 and 14, the barrier layer 24 has a reduced tendency to shift or bunch up within the pantiliner 10. The barrier layer may also be secured in the middle region 16 of the pantiliner 10. When the barrier layer 24 is secured in the middle region 16, the pantiliner 10 is more resistant to liquid strikethrough at the middle region where the greatest amount of protection against staining is required.

As is shown in FIGS. 2 and 3, the pantiliner 10 is preferably provided with an optional topsheet 26. The topsheet 26 is located adjacent to the body-facing side of the core 20. The topsheet 26 may be formed by any soft, smooth, compliant, porous material which will be comfortable against human skin and through which vaginal discharges will tend to pass. Those skilled in the art can readily select woven and nonwoven materials useful for this purpose. In general, porous materials used as topsheets for disposable diapers or as coverings for conventional sanitary napkins can be used in the present invention.

Preferred topsheets include formed thermoplastic films such as those described with particularly in U.S. Pat. No. 4,324,246 issued to Mullane and Smith on Apr. 13, 1982, and U.S. Pat. No. 4,341,217 issued to Ferguson and Landrigan on July 27, 1982. The most preferred topsheets include those described in U.S. Pat. No. 4,342,314, issued to Radel and Thompson on Aug. 3, 1982, as well as U.S. Pat. No. 4,463,045, issued to Ahr, Louis, Mullane, and Oulette on July 31, 1984. These four patents are incorporated herein by reference.

As illustrated in FIGS. 2 and 3, pantiliner 10 is provided with an optional wicking layer 28. The wicking layer 28 is preferably interposed between the core 20 and the topsheet 26, although it is known in the art that the wicking layer 28 may be located in other areas, including on the garment-facing side of the core 20. For example, the wicking layer may be interposed between the barrier layer and the core, or may completely surround the core. Any material which causes vaginal discharges contacting the surface of the pantiliner 10 to migrate along and across the undersurface of the topsheet 26 thereby tending to distribute the vaginal discharges across the whole of the pantiliner 10 can be used. One suitable technique is the provision of a layer of fibers affixed to the inner surface of the topsheet 26 as described in the previously incorporated patent issued to Mullane and Smith. Preferably, wicking layer 28 comprises a sheet of tissue paper closely associated with the inner surface of topsheet 26. Tissue papers used in commonly available tissue products, such as that marketed under the registered trademark BOUNTY by The Procter & Gamble Company of Cincinnati, Ohio can be used. Especially preferred are tissue papers manufactured by either of the processes described in U.S. Pat. No. 3,301,746, issued to Sanford and Sisson on Jan. 31, 1967 and U.S. Pat. No. 3,994,771, issued to Morgan and Rich on Nov. 30, 1976. Both of these two patents are incorporated herein by reference.

Referring to FIGS. 1, 2 and 3 which illustrate a preferred embodiment of the present invention, the topsheet 26, the wicking layer 28, the core 20, the barrier layer 24 and the outer layer 22 are secured to each other about the periphery of the pantiliner 10 with a seal 34. The seal 34 can be achieved by mechanical crimping, thermal welding, ultrasonic welding, adhesives bonding, etc. Although preferably all of the above elements are secured by seal 34, several alternative embodiments are possible whereby some of the elements are not secured to the other elements by the seal 34.

The pantiliner 10 is provided with optional adhesive fastening means 30 as is illustrated in FIGS. 2 and 3. The adhesive fastening means 30 are illustrated as a wide strip running the entire length of the pantiliner 10. This arrangement is selected for convenience; those skilled in the art can readily select a different pattern for the adhesive attachment means.

The purpose of the adhesive attachment means is to secure the pantiliner in the crotch region of the user's undergarment. An adhesive or glue used with sanitary napkins for such purposes can be used with this invention. Pressure sensitive adhesives are preferred. Suitable adhesives include Century A-305 IV manufactured by Century Adhesive Corporation and Instant Lok 34-2823 manufactured by National Starch Company.

Other means for physically securing the pantiliner in the crotch region of the user's undergarment can be used, but adhesive attachment means are preferred.

When adhesive attachment means 30 is present in the device, it is usually covered, prior to the time the user affixes the pantiliner to her undergarment, with a release liner 32. The release liner 32 serves to keep adhesive attachment means 30 from drying out and to keep it from sticking to extraneous surfaces prior to use. Any release liner commonly used for such purposes with sanitary napkins can be used with this invention. Examples of suitable release liners are BL30MG-A SILOX E1-0 and BL30MG-A SILOX 4P/O manufactured by Akrosil Corporation.

EXAMPLE

A pantiliner having the shape illustrated in FIG. 1 and the cross sectional configurations illustrated in FIGS. 2 and 3 is constructed. The topsheet 26 is a formed thermoplastic film as is disclosed in U.S. Pat. No. 4,342,314 issued to Radel and Thompson. The wicking layer 28 comprises a single sheet of tissue paper formed by the process described in U.S. Pat. No. 3,301,746 issued to Sanford and Sisson. The core 20 is a batt of 100% polyester fibers. The barrier layer 24 is a 1.0 mil film of polyethylene which has a uniform width of 48.3 mm. The outer layer is a polypropylene nonwoven material. All of these elements are secured together by a seal 34 achieved by ultrasonic welding. Adhesive attachment means comprising a longitudinal strip of Century A-3051, the adhesive being covered by BL3MG-A SILOX E1-O release liner 32, are used. The pantiliner is about 147.3 mm in length, about 61 mm in transverse width at its widest point, and about 48.3 mm in transverse width at its narrowest point. In use, the pantiliner is found to be comfortable, absorbent, and breathable.

While particular embodiments of the present invention have been illustrated and described, those skilled in the art will recognize that various changes and modifications can be made without departing from the spirit and scope of the invention. It is intended to cover, in the claims, all such modifications that are within the scope of this invention.

What is claimed is:

1. An absorbent article having two end regions, a middle region, and at least one ventilation area positioned adjacent at least one of said end regions wherein body liquids are retained, said absorbent article comprising
    a core having a garment-facing side and a body-facing side;
    a relatively vapor pervious outer layer disposed adjacent said garment facing layer of said core and
    a relatively impervious barrier layer interposed between said core and said outer layer, said barrier layer being substantially liquid, vapor and air impermeable;
    wherein said barrier layer is substantially longitudinally coterminous with said absorbent; article and is of a relatively smaller transverse width than at least one of said end regions so as to form said ventilation area.

2. The absorbent article of claim 1 wherein said barrier layer has a uniform transverse width.

3. The absorbent article of claim 2 wherein said barrier layer is secured to said core and said outer layer at said end regions.

4. An absorbent article having two end regions, a middle region, and at least one ventilation area adjacent at least one of said end regions; wherein said absorbent article tapers inwardly from a relatively greater transverse width at at least one of said end regions to a relatively smaller transverse width in said middle region, said absorbent article comprising:
- a core;
- a relatively vapor pervious outer layer adjacent said core; and
- a relatively impervious barrier layer interposed between said core and said outer layer, said barrier layer being substantially liquid, vapor and air impermeable;
- wherein said barrier layer is substantially longitudinally coterminous with said absorbent article and is of a relatively smaller transverse width than at least one of said end regions so as to form said ventilation area.

5. The absorbent article of claim 4 wherein said barrier layer has a uniform transverse width.

6. The absorbent article of claim 5 wherein said barrier layer is secured at said end regions.

7. An absorbent article having two end regions, a middle region, and at least one ventilation area positioned adjacent at least one of said end regions; wherein body liquids are retained said absorbent article tapers inwardly from a relatively greater transverse width at said end regions to a relatively smaller transverse width in said middle region, said absorbent article comprising:
- a core having a garment-facing side and a body-facing side;
- a relatively vapor pervious outer layer disposed adjacent said garment-facing side of said core; and
- a relatively impervious barrier layer interposed between said core and said outer layer, said barrier layer being substantially liquid, vapor and air impermeable;
- wherein said barrier layer is substantially longitudinally coterminous with said absorbent article and is of a relatively smaller transverse width than said end regions so as to form said ventilation area.

8. The absorbent article of claim 7 wherein said barrier layer has a uniform transverse width.

9. The absorbent article of claim 8 wherein said barrier layer is substantially the same transverse width as said middle region.

10. The absorbent article of claim 9 wherein said barrier panel layer is secured at said end regions.

11. The absorbent article of claim 10 wherein said barrier layer is secured at said middle region of said absorbent article.

12. The absorbent article of claim 11 wherein said absorbent article tapers nonlinearly inwardly from a relatively greater transverse width at said ends to a relatively lesser transverse width in said middle section.

13. The absorbent article of claim 7 wherein said barrier layer comprises a thermoplastic film.

14. The absorbent article of claim 7 wherein said outer layer comprises a nonwoven web.

15. The absorbent article of claim 7 wherein said core comprises a batt of polyester fibers.

16. The absorbent article of claim 7 wherein said absorbent article further comprises a liquid pervious topsheet adjacent said core.

17. The absorbent article of claim 16 wherein said liquid pervious topsheet is a formed thermoplastic film.

18. The absorbent article of claim 16 wherein said absorbent article further comprises a wicking layer interposed between said liquid pervious topsheet and said core.

19. The absorbent article of claim 16 wherein said absorbent article further comprises a wicking layer interposed between said barrier layer and said core.

20. The absorbent article of claim 7 wherein said absorbent article further comprises adhesive attachment means affixed on said outer layer.

21. An absorbent article having two end regions, a middle region, and at least one ventilation area adjacent at least one of said end regions; wherein said absorbent article tapers nonlinearly inwardly from a relatively greater transverse width at said end regions to a relatively smaller transverse width in said middle region, said absorbent article comprising:
- a core having a garment-facing side and a body-facing side;
- a relatively vapor pervious outer layer adjacent said garment-facing side of said core; and
- a relatively impervious barrier layer interposed between said core and said outer layer, said barrier layer being substantially liquid, vapor and air impermeable;
- wherein said barrier layer is substantially longitudinally coterminous with said absorbent article and has a uniform transverse width that is substantially the same transverse width as said middle region and of a relatively smaller transverse width than said end regions so as to form said ventilation area;
- a liquid pervious topsheet adjacent said body-facing side of said core;
- a wicking layer interposed between said liquid pervious topsheet and said core; and
- an adhesive attachment means affixed on said outer layer.

22. The absorbent article of claim 21 wherein said barrier layer is secured at said end regions of said absorbent article.

23. The absorbent article of claim 22 wherein said barrier layer is secured at said middle region of said absorbent article.

24. The absorbent article of claim 23 wherein said barrier layer comprises a thermoplastic film.

25. The absorbent article of claim 24 wherein said outer layer comprises a nonwoven web.

26. The absorbent article of claim 25 wherein said core comprises a batt of polyester fibers.

27. The absorbent article of claim 26 wherein said liquid pervious topsheet is a formed thermoplastic film.

28. The absorbent article of claim 27 wherein said wicking layer comprises tissue paper.

* * * * *